(12) United States Patent
Bula (10) Patent No.: US 7,565,768 B2
(45) Date of Patent: Jul. 28, 2009

(54) CONTROLLED ENVIRONMENT SYSTEM AND METHOD FOR RAPID PROPAGATION OF SEED POTATO STOCKS

(75) Inventor: Raymond J. Bula, Cross Plains, WI (US)

(73) Assignee: CETS, LLC, Sussex, WI (US)

( * ) Notice: Subject to any disclaimer, the term of this patent is extended or adjusted under 35 U.S.C. 154(b) by 0 days.

(21) Appl. No.: 12/256,987

(22) Filed: Oct. 23, 2008

(65) Prior Publication Data

US 2009/0077883 A1    Mar. 26, 2009

Related U.S. Application Data

(62) Division of application No. 11/451,272, filed on Jun. 12, 2006, now Pat. No. 7,472,513.

(60) Provisional application No. 60/758,313, filed on Jan. 12, 2006.

(51) Int. Cl.
*A01G 1/00* (2006.01)
*A01G 31/00* (2006.01)

(52) U.S. Cl. ................ 47/89; 47/58.1 LS; 47/60; 47/62 R; 47/DIG. 6

(58) Field of Classification Search .......... 47/58.1 R, 47/58.1 LS, 17, 60, 61, 62 R, 62 A, 62 N, 47/89, DIG. 3; 435/429, 420
See application file for complete search history.

(56) References Cited

U.S. PATENT DOCUMENTS

| | | |
|---|---|---|
| 3,424,231 A | 1/1969 | Truhan |
| 3,746,080 A | 7/1973 | Mallory |
| 4,091,566 A | 5/1978 | Horvath et al. |
| 4,196,544 A | 4/1980 | Davis et al. |
| 4,860,490 A | 8/1989 | Morris et al. |
| 5,047,343 A | 9/1991 | Joyce et al. |
| 5,049,505 A | 9/1991 | Sei |
| 5,111,612 A | 5/1992 | Takishima et al. |
| 5,269,093 A | 12/1993 | Horaguchi et al. |
| 5,282,873 A | 2/1994 | Watari |
| 5,283,974 A | 2/1994 | Graf, Jr. |
| 5,413,929 A | 5/1995 | Ishizaki et al. |

(Continued)

FOREIGN PATENT DOCUMENTS

EP    0 655 192 A2    5/1995

(Continued)

OTHER PUBLICATIONS

International Search Report mailed Jan. 15, 2007 in corresponding PCT Application No. PCT/US2006/025235.

(Continued)

*Primary Examiner*—T. Nguyen
(74) *Attorney, Agent, or Firm*—Andrus, Sceales, Starke & Sawall, LLP (57) ABSTRACT

A computer controlled environment system and method are used to provide the optimum environmental and nutritional conditions for the growth and development of seed potato cuttings for the initiation and development of tubers that can be used as the seed source for further multiplication under field conditions as seed potato stock. Use of a controlled environment system and method that provides optimum cultural conditions results in rapid growth and development of the potato cutting so as up to six crops of tubers can be harvested in a calendar year.

7 Claims, 8 Drawing Sheets

U.S. PATENT DOCUMENTS

| | | |
|---|---|---|
| 5,419,079 A | 5/1995 | Wang et al. |
| 5,493,808 A | 2/1996 | Munday |
| 5,498,541 A | 3/1996 | Oka et al. |
| 5,854,066 A | 12/1998 | Oka |
| 5,946,853 A | 9/1999 | Jacobs et al. |
| 6,071,746 A | 6/2000 | Seabrook et al. |
| 6,088,958 A | 7/2000 | Oka et al. |
| 2005/0076563 A1 | 4/2005 | Faris |
| 2005/0252078 A1 | 11/2005 | Albright et al. |

FOREIGN PATENT DOCUMENTS

| | | | |
|---|---|---|---|
| WO | 0057688 A2 | 10/2000 | |

OTHER PUBLICATIONS

Gutknecht, K., Space science, Chinese ingenuity speed up potato development, Agriculturist, Feb. 1999, SP-002410701.

Wisconsin Company Develops Revolutionary Production Technology for Seed Potatoes, Jan. 3, 2000; pp. 1-2; XP-002410702 (URL:www.ag-tec.com/pruir.htm).

Tibbitts, T. et al; Cultural Systems for Growing Potatoes in Space, ACTA Horticulturae (Wageningen) No. 230, 1988; pp. 287-290; XP008072545 and International Symposium on High Hamamatsu, Japan, May 12-15, 19, ISSN: 0567-7572.

CONTROLLED ENVIRONMENT SYSTEM AND METHOD FOR RAPID PROPAGATION OF SEED POTATO STOCKS

CROSS REFERENCE TO RELATED APPLICATION

This application is a divisional of U.S. Ser. No. 11/451,272, filed Jun. 12, 2006, which application claims priority based on U.S. Provisional Patent Application Ser. No. 60/758,313 filed Jan. 12, 2006.

FIELD OF THE INVENTION

This invention relates to the growth of potato tubers using a system of controlled environments that provides the optimum environmental and nutritional conditions for the growth and development of potato plants and tuberization. These tubers form the basic material that can be further propagated under field conditions into large quantities of high quality seed potato stocks.

BACKGROUND OF THE INVENTION

The potato is the world's foremost important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C. The U.S. acreage planted in potatoes has declined since the 1960's and 1970's, and this decline, coupled with increasing consumption, must be offset by higher usable yields. In some areas, diseases and pests damage crops despite the use of herbicides and pesticides.

It is generally recognized that quality seed potato stocks, usually identified as "Certified Seed", are an essential component of profitable potato production enterprises. The use of such seed stocks is critical to the financial success of these enterprises because potatoes are one of the few vegetatively propagated crop species. Consequently, any disease introduction into the seed potato stock material is present in all successive propagations with its consequent deleterious impact because the potato tuber is a vegetative organ rather than a seed organ.

A number of schemes have been developed to minimize the impact of diseases on the commercial value of seed potato stocks. Such schemes are based on starting with tissue cultures of disease-free material in a sterile laboratory environment followed by growing out these established tissue cultures in greenhouse or outdoor screenhouse conditions. These schemes are described in a number of articles in the potato research literature including Struik, 1991, Struik and Wiersma, 1999, and Pruski, et al, 2003. A slightly different scheme is used by the Wisconsin Seed Potato Certification Program Department of Plant Pathology, University of Wisconsin-Madison, 1630 Linden Drive, Madison, Wis. 53706, for the generation of "Elite Foundation Seed" and subsequent sale to certified seed potato growers. This involves the identification of pathogen-negative material that is maintained on long-term tissue culture media in the form of microtubers. Each year, these "clones" are subcultured into thousands of plants, which are planted in a protected screenhouse for generation of tubers. These tubers are further propagated in the field and become the "Elite Foundation Seed".

The schemes described in the published literature have several inherent limitations. These limitations include, limiting the amount of seed stock material that can be produced in any given calendar year, and the cost of producing such seed stock material. The greenhouse-based schemes provide at most two tuber harvests per year, even in geographic regions where the winter months of the year are not too cold. The screenhouse based schemes are limited essentially to only one tuber harvest per year. Both the greenhouse and screenhouse schemes have a high degree of probability of inadvertent insect infestation, such as aphids and leafhoppers that are vectors of serious potato diseases. The low production results of the schemes also reduce the availability of sizable seed stocks of new cultivars to commercial potato enterprises.

A method for producing potato minitubers is known from U.S. Pat. No. 5,419,079 issued May 30, 1995 to Wang et al. This patent sets forth a multiplicity of procedural method steps affecting the environmental and nutritional conditions of potato cuttings being propagated. This scheme, however, requires that all method steps are performed manually and without any automatic monitoring and control of the environment so that it is highly labor intensive and totally non-reactive. In addition, the cuttings must be placed in a shed built with frames and plastic film in a greenhouse after which the film is manipulated, all of which is cumbersome and inefficient. All control of temperature, lighting, humidity and nutrients occurs without any feedback during the propagation process. It is questionable that such manually controlled scheme will produce in a consistent and fast manner and without complications, as claimed, particularly in any geographic location.

Other computerized plant growing systems are known, but none are designed to optimize growth of potato plants over an entire life cycle.

SUMMARY OF THE INVENTION

It is a general object of the present invention to provide a system for and method of more efficiently propagating seed potato stocks by automatically monitoring, controlling and recording environmental and nutritional parameters within a chamber arrangement in which potato plants are grown and developed.

The controlled environment system and method provide optimum environmental and nutritional growing conditions so that the potato plants produce harvestable tubers in less than 60 days from planting. Such rapid growth cycles allow for up to six harvests per year in any geographic location. The environmental conditions are controlled and recorded inside a unique chamber and include the duration and intensity of light, the air temperature during the light and dark periods, and the humidity level of the atmosphere in which the plants are growing. Additionally, the composition of the nutrients and water provided to the plant is programmed during the growth cycle to correspond to the nutrient requirements during the specific stage of development of the potato plant and tuberization. Thus, a carefully synchronized, environmental and nutritional regime supports rapid growth and development so that the six tuber harvests can be made during any calendar year, regardless of the outdoor weather conditions where the controlled environment system is operating. The tubers produced in the controlled environment chamber are subsequently multiplied via tuber field plantings to produce a sufficient quantity of high quality certified seed potato material for sale to potato growers.

In one aspect of the invention, a plant growing system is provided for developing potato plants that produce minitubers. The system includes at least one automatically controlled environment chamber structure for holding and supporting growth of potato plants over an entire life cycle. The chamber structure includes temperature, humidity and light sensor devices, a lighting structure for establishing light and dark periods of exposure and having a number of florescent lamps located above the potato plants and separated therefrom by a substantially transparent divider. An air temperature structure including an air conditioner is provided for creating a variable temperature uniformly throughout the chamber structure. An atmospheric humidity structure maintains a relative humidity throughout the chamber structure, and a nutrient and water delivery structure is provided for fertilizing and irrigating the potato plants. A computer is provided for automatically and continuously monitoring and controlling the lighting, air temperature, atmospheric humidity and nutrient and water delivery structure. The system enables development of both tissue culture plantlets into mother plants, and stem cuttings from the mother plants that produce minitubers. The computer also periodically records environmental parameters in the chamber structure.

The invention also contemplates a method for developing potato plants that produce minitubers. The method includes the step of providing at least one automatically controlled environment chamber structure for holding and supporting growth of potato plants over an entire life cycle, the chamber structure including temperature, humidity and light sensor devices, lighting structure for establishing light and dark periods of exposure having a number of florescent lamps located above the potato plants and separated therefrom by a substantially transparent divider, and air temperature structure including an air conditioner for creating a variable temperature uniformly throughout the chamber structure, an atmospheric humidity structure, a nutrient and water delivery structure for fertilizing and irrigating the potato plants, and a computer for automatically and continuously monitoring and controlling the lighting, air temperature, atmospheric humidity and nutrient and water delivery structures, and periodically recording status of various environmental parameters in the chamber structure; placing uncovered stem cuttings from mother plants within trays supplied with a solid growth medium inside the chamber structure in a single layer; culturing the stem cuttings in the chamber structure into minitubers by automatically monitoring and controlling the duration and intensity of the lighting, air temperature as a function of time during the light and dark periods, the percentage of humidity as a function of time, and the duration and frequency of aqueous nutrients according to set points established in the computer as compared with inputs from the sensor devices; and harvesting the minitubers in 56-64 days of culturing.

BRIEF DESCRIPTION OF THE DRAWINGS

The drawings illustrate the best mode presently contemplated of carrying out the invention.

In the drawings.

DETAILED DESCRIPTION OF THE INVENTION

General Overview

Figure 1:
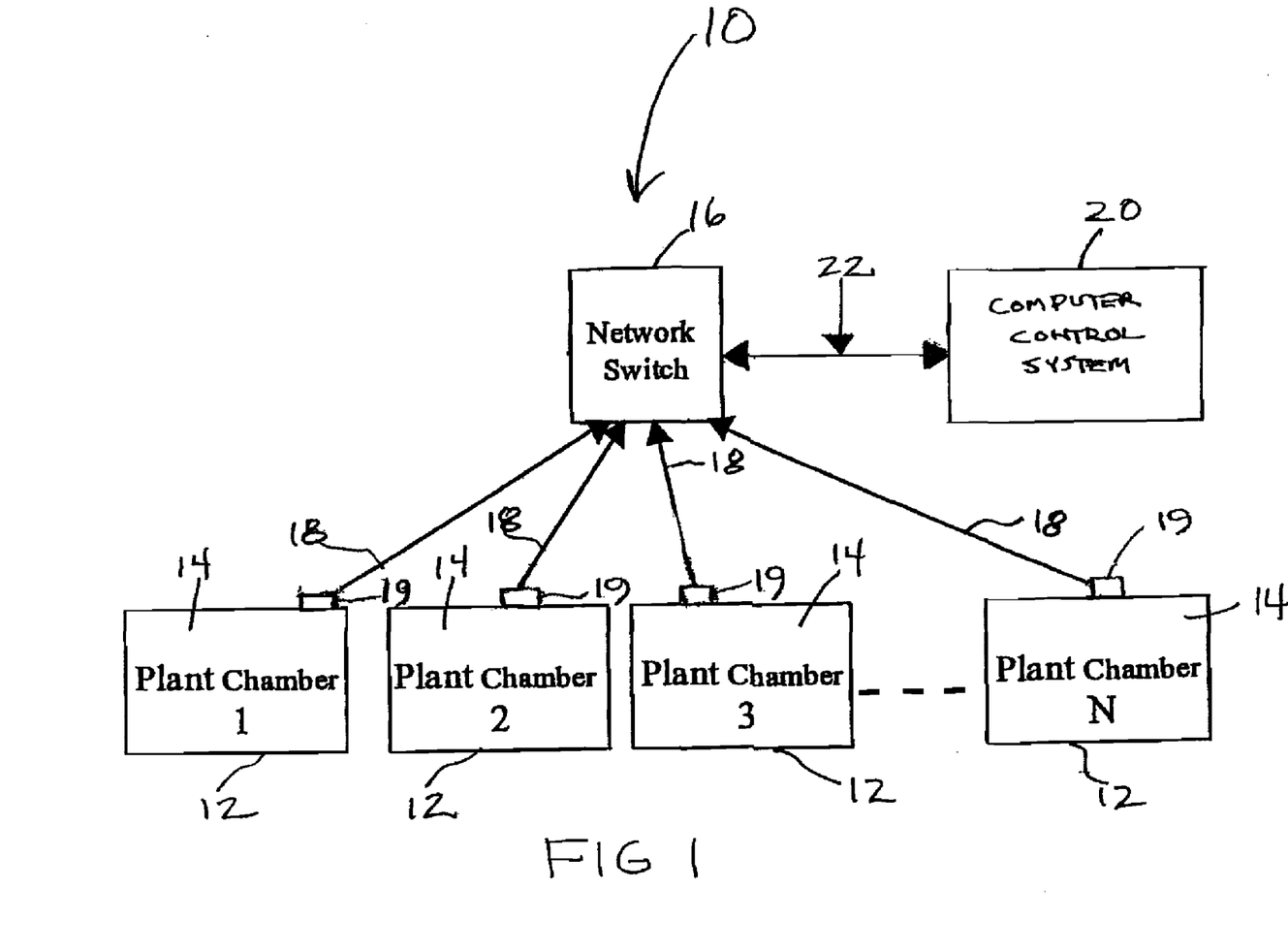
FIG. 1 is a block diagram of an environmental monitoring and control system for propagating seed potatoes.

Referring now to the drawings, FIG. 1 illustrates an environmental and control system 10 for propagating seed potatoes in accordance with the present invention. The system 10 is comprised generally of at least one and preferably a plurality of housings 12 forming plant chambers 14 for nurturing and developing seed potatoes and supporting tuberization. The housings 12 and their chambers 14 are in communication with a network switch 16 by means of several Ethernet connectors 18 that are connected to control panels 19 associated with the chambers 14. The network switch 16 is also in communication with a computer control system 20 due to further Ethernet connection 22. As will be understood hereafter, the computer control system 20 has software which automatically and continuously monitors and controls several critical systems inside the chamber 14, and periodically records the status of environmental conditions therein in order to optimize the rapid growth and tuberization of the potato plants.

The critical components of each chamber 14 that provide the optimum controlled environment for potato plant growth and development include:

1. A lighting system 24 capable of providing the level of light intensity that results in a photosynthetic rate sufficient to produce tuberization of the potato plants growing in the chamber 14. The lighting system 24 can be comprised of florescent lamps, light emitting diodes or other lights 26 placed closely adjacent the potato plants.

2. An air temperature system 28 capable of providing the desired air temperature that results in rapid plant growth and also supports tuberization of the potato plants. The air temperature system 28 is generally comprised of an air conditioner 30 positioned on the housing 12.

3. An atmospheric humidity delivery system 32 capable of providing the humidity conditions in the surrounding atmosphere required to support rapid plant growth rates and tuberization of the potato plants.

4. A nutrient and water delivery system 34 capable of providing foliar applications of the fluid nutrients required to support rapid plant growth and tuberization of the potato plants.

5. A computer control system 20 having a computer capable of monitoring and controlling the desired level and duration of light, the desired air temperature, the atmospheric humidity conditions and the proper nutrient and water delivery during prescribed stages of development and tuberization. The computer control system 20 is further capable of recording the status of environmental parameters in the chambers 14 at various selected times.

Figure 2:
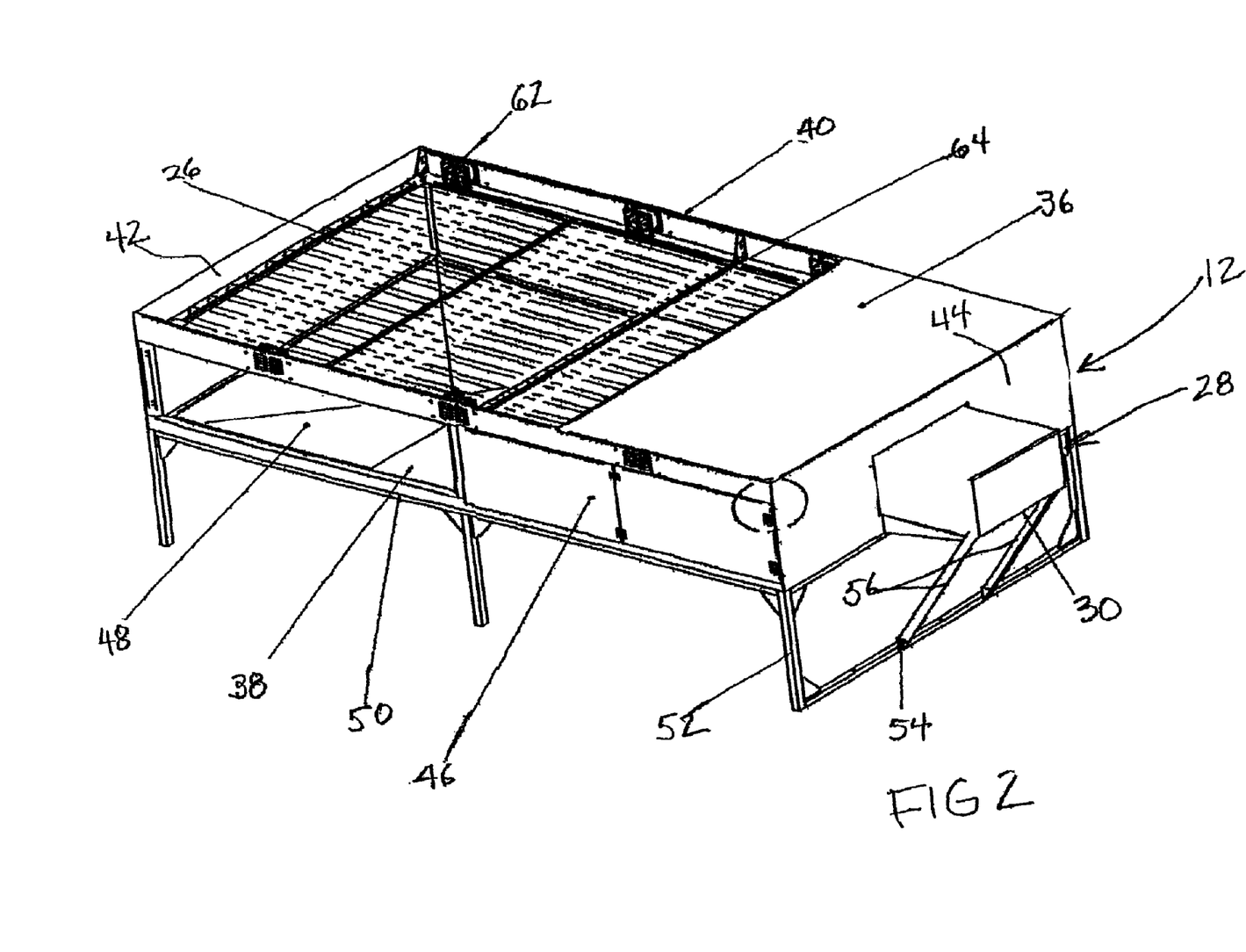
FIG. 2 is a fragmentary, perspective, broken away view of a controlled environment chamber used in the system of FIG. 1.
Figure 2A:
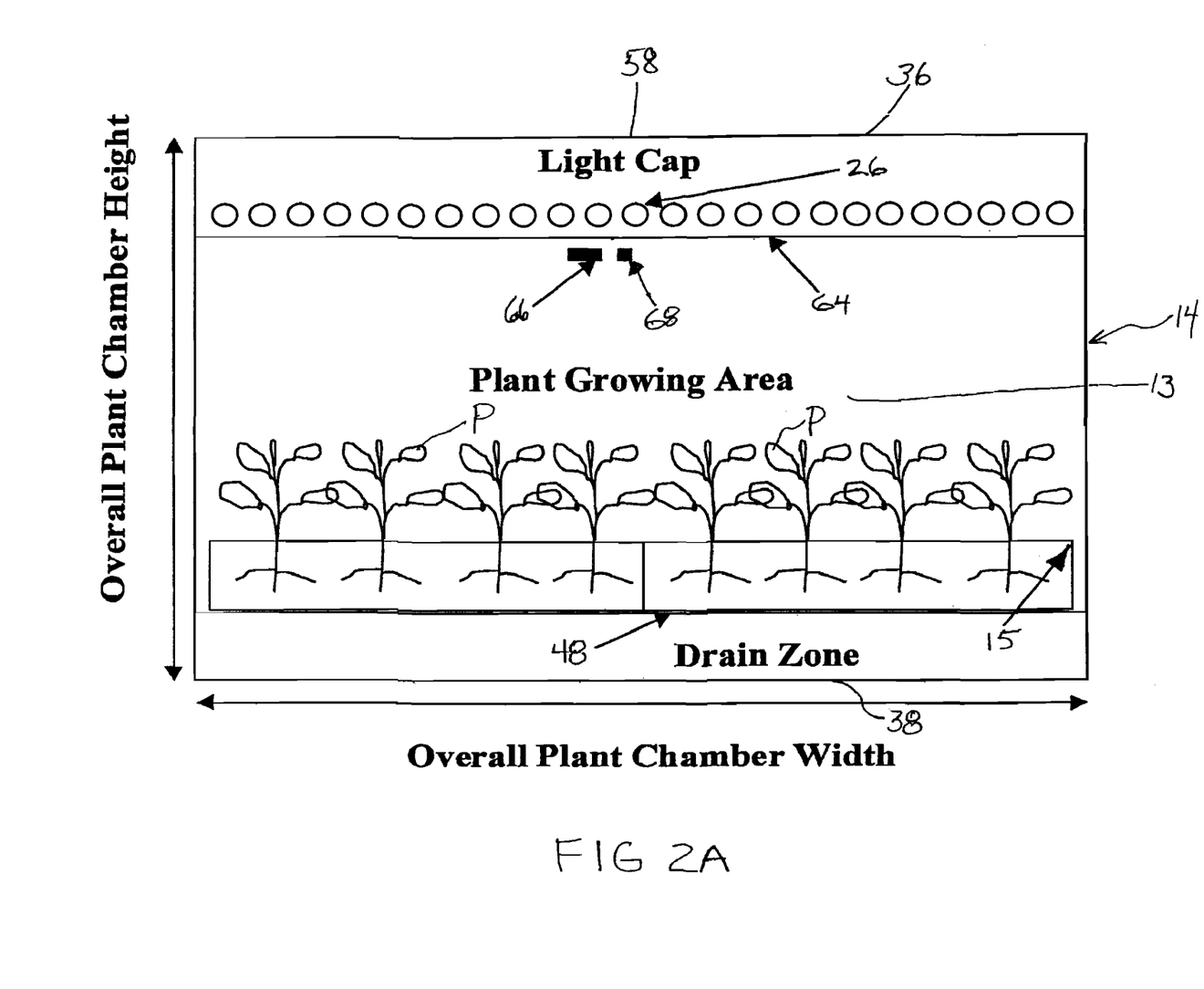
FIG. 2A is a sectional representation of a portion of the chamber in FIG. 2.
Figure 4:
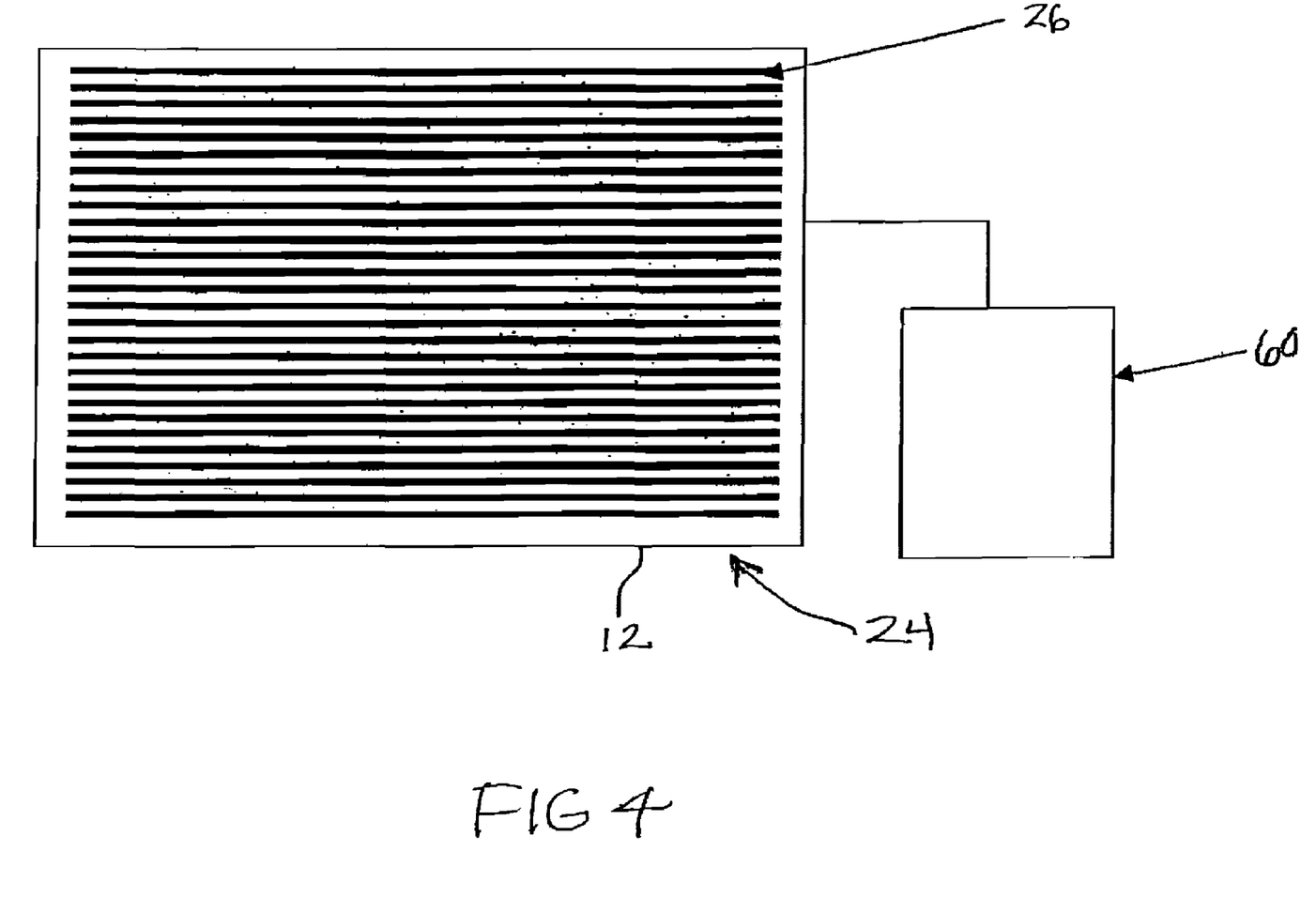
FIG. 4 is a block diagram of a lighting system used in connection with the chamber in FIG. 2.

Referring now to FIGS. 2 and 2A, there shown is the typical housing 12 forming each growing area 13 and plant chamber 14. Each housing 12 includes a solid top panel 36, a solid bottom panel 38, a solid back panel 40, solid opposite end panels 42, 44, and a pair of movable chamber doors, one being seen at 46. Typical outside dimensions of the housing 12 are four and one-half feet in width, nine feet in length and three feet in height. Housing 12 is normally a confined environment when doors 46 are closed. Bottom panel 38 is provided with a drain pan 48 and is supported about three feet above a support surface by a framework 50 having a number of depending legs 52. One end of the housing 12 includes a horizontal member 54 interconnected between the legs 52. The horizontal member 54 serves as a connection point for a pair of braces 56 that support the air conditioner 30 mounted on end panel 44 for controlling the temperature of air inside the chamber 14. A plurality of florescent lamps 26 are positioned across the upper portion of the chamber 14 beneath the top panel 36. The lamps 26 are enclosed in a light cap 58 (FIG. 2A) defined by the highly reflective top panel 36, a substantially transparent acrylic plastic sheet 64 and the end panels 42, 44. The sheet 64 forms the bottom of the light cap 58 and also serves as the ceiling for the plant growing area 13 in chamber 14. The lamps 26 are connected to a lamp ballast 60 located outside the housing 12 as represented in FIG. 4. Ventilating fans 62 are provided at the front and back upper portions of housing 12. Typically, the doors 46 are opened to permit the sliding of trays 15 with plant seedlings P into and out of the chamber 14.

Figure 3:
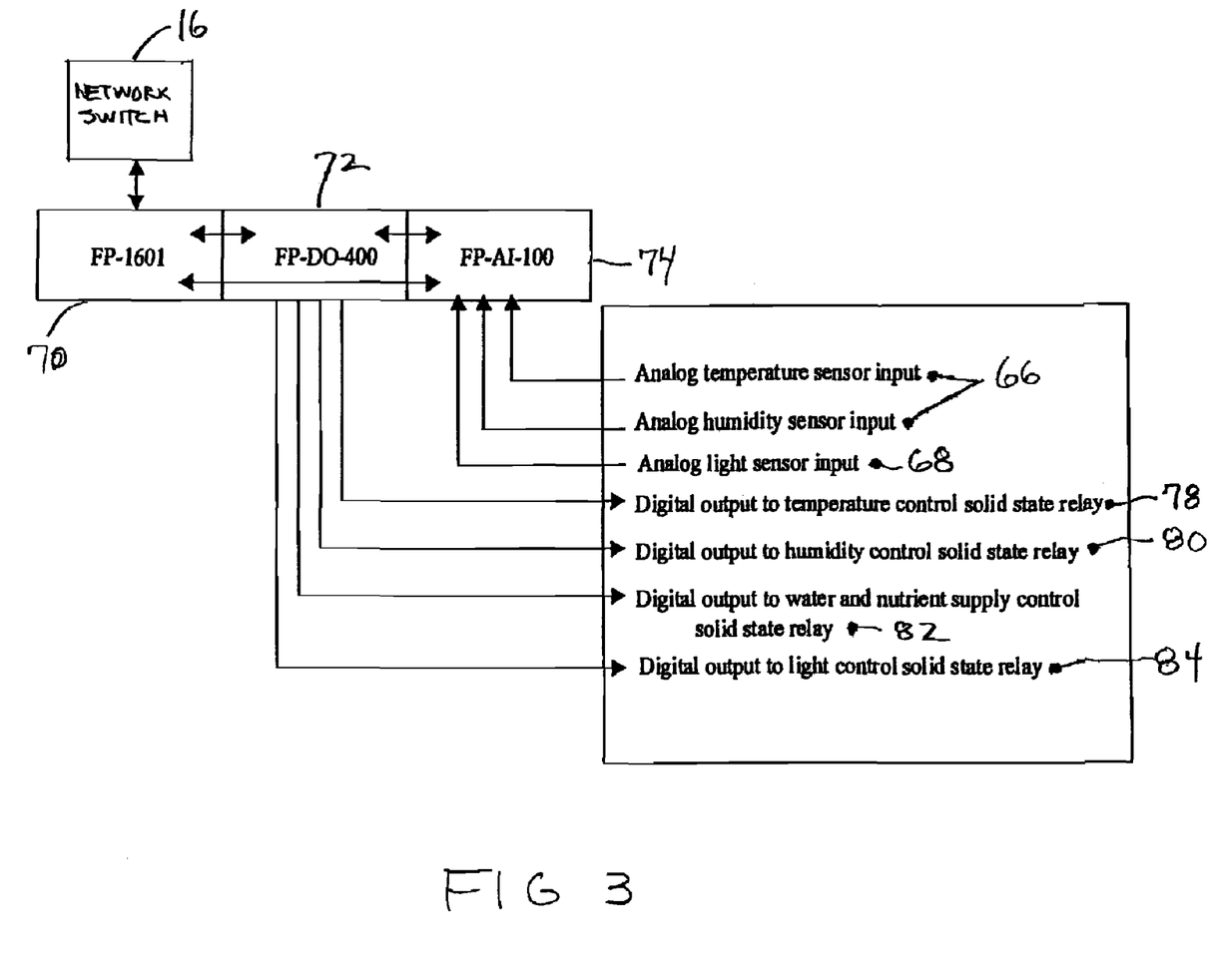
FIG. 3 is a more detailed block diagram of the computer control system for FIG. 1.

As seen in FIG. 3, each housing 12 is provided with a combined analog temperature/humidity sensor 66 and an analog light sensor 68. The sensors 66, 68 are typically centrally located on a wall of the housing 12 approximately three inches below the acrylic sheet 64. The combined sensor 66 monitors the air temperature and humidity levels in the chamber 14 and continuously feeds back these parameters to a first of three signal interface modules 70, 72, 74 in communication with an Ethernet connector 76 to the network switch 16. The modules 70, 72, 74 are contained in each control panel 19. The light sensor 68 simply provides a verification that the lights 26 are on or off. The number of lamps 26 to be illuminated and the length or duration of the light period are determined by the operator for any desired growth condition. The light sensor 68 does not turn on or turn off any lamps 26. The housing 12 further is provided with a digital temperature control relay 78, a digital humidity control relay 80, a digital light control relay 82 and a digital nutrient supply control relay 84. All these relays 78, 80, 82, 84 communicate with the second signal interface module 72 and respond according to the sensor 66. The module 74 functions as a microprocessor and interfaces with software in the control computer. The module 74 compares the sensor output of the module 70 to desired set points in the software, and then passes on appropriate information to the module 72 which, in turn, activates the appropriate relays 78, 80, 82, 84 to affect starting or stopping the specific unit that provides the desired environmental conditions in the chamber 14.

Figure 5:
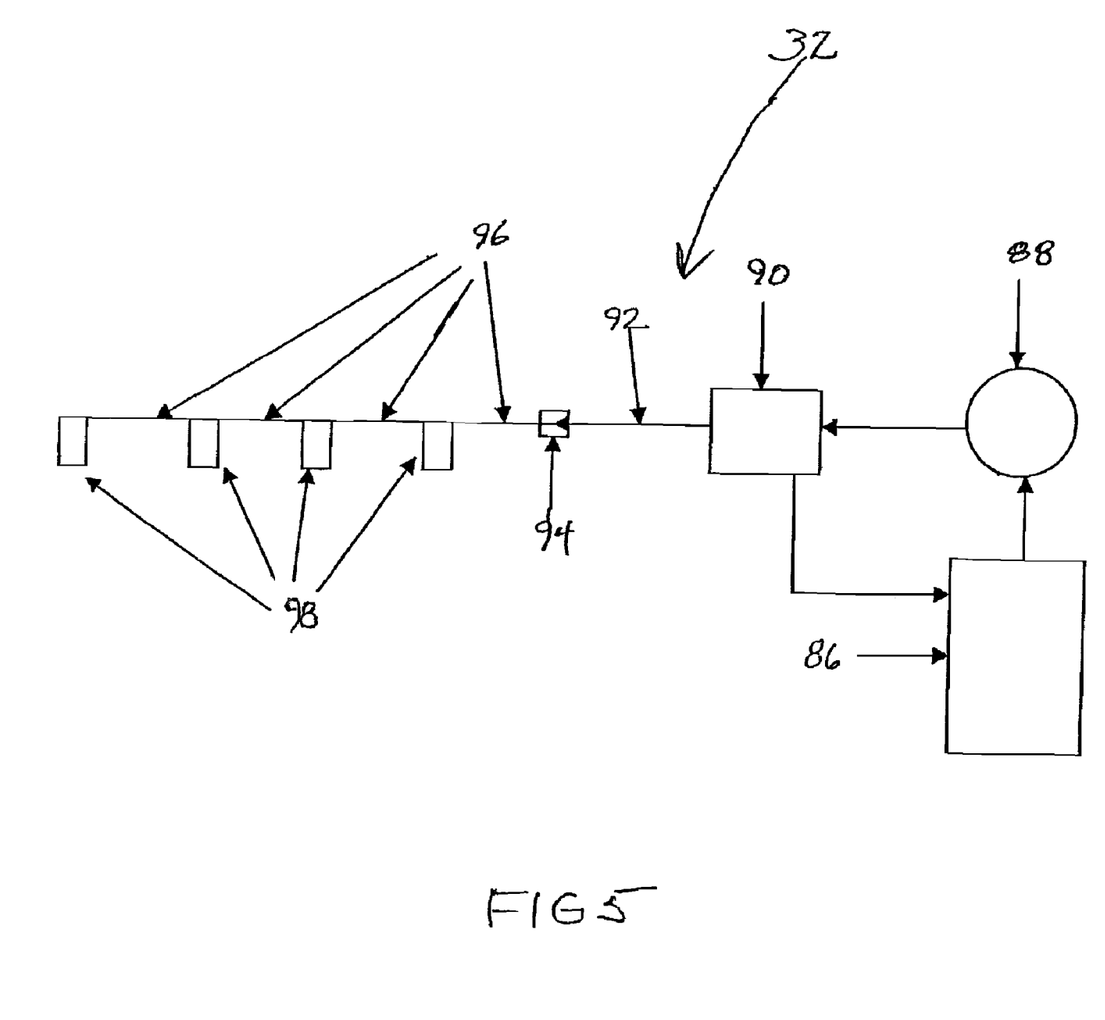
FIG. 5 is a block diagram of an atmospheric humidity system used with the chamber of FIG. 2.

FIG. 5 depicts the atmospheric delivery system 32 for each housing 12. The humidity delivery system 32 includes a humidity solution reservoir 86 connected to a pump 88 and a pressure relief valve 90, all of which are located outside the housing 12 and chamber 14. A hose 92 secured to the pressure relief valve 90 runs inside the chamber 14, and is joined by a connector 94 to a pipe 96 having a series of spaced apart misting nozzles 98 extending into the chamber 14 for controlling humidity therein.

Figure 6:
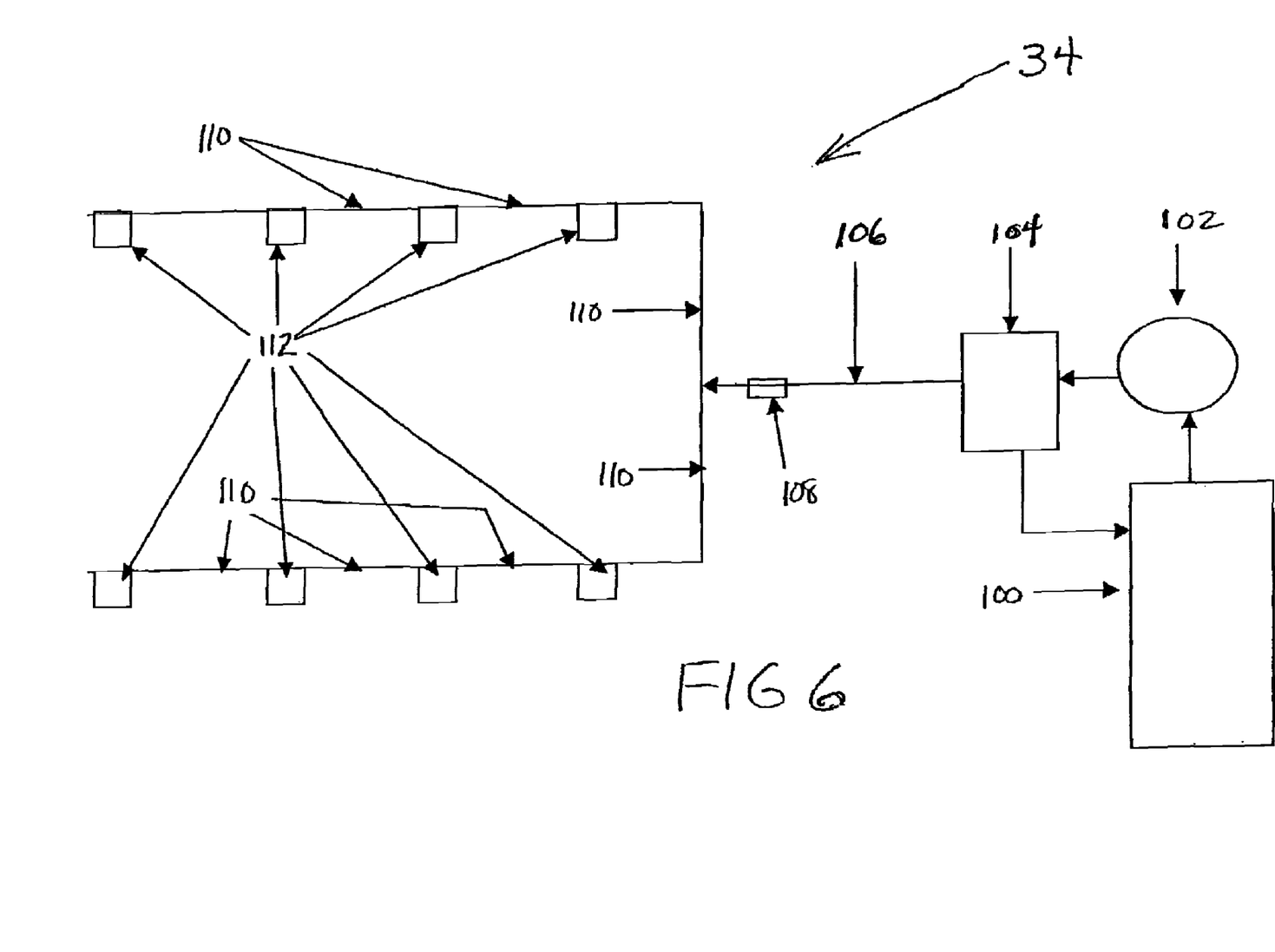
FIG. 6 is a block diagram of a nutrient and water delivery system used in the chamber of FIG. 2.

FIG. 6 represents the nutrient delivery system 34 for each housing 12. The nutrient delivery system 34 includes a nutrient solution reservoir 100 joined to a pump 102 and a pressure relief valve 104, all of which lie outside the housing 12 in chamber 14. Similar to the humidity delivery system 32, a hose 106 secured to the pressure relief valve 104 runs inside the chamber 14, and is joined by a connector 108 to a pipe 110 having a series of spaced apart misting nozzles 112 for delivering nutrients into the chamber 14.

System Details

Plant Growing Area

The plant growing area 13 (FIG. 2A) has a height of approximately 2 feet which allows for sufficient plant growth height while at the same time keeps the distance between the lights 26 and the plants P to a minimum. The distance from the lamps 26 to the plants P is a critically important design feature so as to maximize the amount of light incident on the plant leaves. Fundamental physics (Beer's Law) states that the intensity of light at any point perpendicular to the source of the light is inversely related to the square of the distance from the light source. Thus, in order to maximize the efficiency of the light system 24, the distance between the light source 26 and the plant leaves must be as short as possible while providing the height dimension that would accommodate the plants P to be grown in the chamber 14. The distance from the lamps 26 to the plant leaves at the beginning of the growth period is approximately 20 inches. As the plants P grow, the distance is reduced to about 6 inches between the lamps 26 and the plant leaves.

The ceiling of the plant growing area 13 is the acrylic sheet 64 that has a high transmission of visible light from the light source 26 into the plant growing area 13. The floor 48 of the plant growing area 13 is perforated metal with sufficient strength to support plant and rooting material in containers 15 while at the same time allowing for drainage of any liquid material that may emanate from the containers 15 housing the rooting material.

Light Cap

The light cap 58 houses the fluorescent lamps 26 used for providing the required radiant energy (light) for the photosynthetic process involved in converting the radiant energy to chemical energy by the plants P. The fluorescent lamps 26 convert electricity to light that can be absorbed by the plant leaves and used in the photosynthetic process. This conversion efficiency is approximately 20 percent, that is 20 percent of the electricity used by the fluorescent lamps 26 is light and the other 80 percent is radiated as heat, mostly as sensible heat. Thus, another critically important design feature of the area of the light cap 58 is that the height be approximately 6 inches so that the light cap 58 forms a "plenum". Air can then be forced through the light cap 58 to remove most of the sensible heat emanating from the fluorescent lamps 26 rather than passing to the plant growing area 13 and thereby burdening the temperature control of the plant growing area 13.

The floor of the light cap 58 is the acrylic sheet 64 that is the plant growing area ceiling. The top panel, or ceiling 36, of the light cap 58 is a highly reflective metal material. Use of a highly reflective material is critically important because fluorescent lamps 26 emit light over the entire 360 degrees of the surface of the fluorescent tube. Since the surface of the growing plants P is perpendicular to the fluorescent lamps 26, it is important the light being emitted from the lamp surface that is away from the plant leaves be reflected back toward the direction of the plant leaves. To further increase the electrical efficiency of the lighting system 24, electronic ballasts 60 are used to power the fluorescent lamps 26.

Another critically important design feature of the light cap area is the use of the fans 62 to move the sensible heat generated by the fluorescent lamps 26 via convection. This feature maintains the lamps 26 at the optimum air temperature of approximately 110 degrees F. Removing the sensible heat emanating from the fluorescent lamps 26 is energy efficient as well as minimizing the impact on the air temperature of the plant growing area 13 since the air temperature of the plant growing area 13 needs to be maintained in the range of 65 to 75 degrees F., depending on the stage of plant development.

The criterion used in selecting the fluorescent lamp 26 is based entirely on the conversion efficiency of the lamp as defined by lumens per watt. This factor is why the plant growing area 30 has a length of essentially 8 feet. Thus, the overall dimensions of the light cap are 9 feet long (8-foot lamps), 4 feet wide and 6 inches high.

Drain Area

The drain area of the chamber 14 is below the floor 38 of the plant growing area 13 and serves to collect any liquid emanating from the plant growing area 13 allowing for convenient disposal of such liquid. Collection and disposal of the liquid is necessary to avoid accumulation of the waste liquid and thereby become a source of deleterious microbial infestations in and around the chamber 14.

Lighting System

The lighting system 24 consists of the fluorescent lamps 26 and the ballasts 60 to drive the lamps (FIG. 4). The fluorescent lamps 26 used to provide the radiant energy required by the plant photosynthetic process are T-8, High Output (HO, 8 feet in length). These lamps 26 provide the highest efficiency of conversion of electricity to visible light of any commercially available fluorescent lamp 26, as expressed by the term "lumens per watt".

The fluorescent lamps 26 are driven by electronic ballasts 60, capable of operating over the range of 120 to 270 VAC. Use of electronic ballasts 60 further increases the total efficiency of the lighting system 24 to convert electricity to visible radiation (light). Likewise, the ability of the ballast 60 to function over a range of voltage inputs allows the use of the lighting system 24 in a variety of environments. The ballasts 60 are housed in an enclosure attached to one of the outside walls of the chamber 14. This reduces the impact heat generated by the ballasts 60 during their operation on the air temperature in the plant growing area 13 of the chamber 14.

The use of commercially available T-8 HO fluorescent lamps 26 and electronic ballasts 60 is a very important design criteria that impacts both the initial and maintenance costs of the plant chamber 14 and the electrical operational costs. Also, the use of fans 62 to remove the sensible heat generated by the fluorescent lamps 26 in the light cap 58 significantly reduces operational costs compared to the use of mechanical refrigeration to remove the sensible heat. These design features are significant considerations that impact the commercial viability of using controlled environmental chambers 14 for the production of pre-basic seed potato material.

The on-off cycle of the lighting system 24 is controlled by inputs into the computer 20 that controls the environmental conditions in the plant growing area 13 of the chamber 14. The controls define when the fluorescent lamps 26 are on and for how long during any 24-hour time cycle. Also, the controls define whether one-third, two-thirds, or, all of the lamps 26 are on, thereby defining the level of radiant energy (light) incident on the plants P growing in the chamber 14. The ability to control the number of lamps 26 that are on at any one time is an important condition for providing the correct level or intensity of light at any specific stage of plant growth and development.

Air Temperature System

The air temperature system 28 is based on the use of the commercially available room air conditioner 30 of sufficient BTU capacity, modified so that the air temperature in the plant growing area 13 can be controlled over the range of 50 to 86 degrees F. (10 to 30 degrees C.). The air conditioner modifications allow the air conditioner 30 to provide cooling in the plant growing area 13 down to 50 degrees F. because all commercially available room air conditioners are configured to limit air temperature control to a minimum of 60 degrees F.

Air temperature in the plant growing area 13 of the chamber 14 can be programmed to provide a different air temperature level during the light and dark periods of a 24-hour cycle. Another feature of the air temperature system 28 relates to the control span, which can be adjusted over the range of ±1 to 4 degrees F. (±0.5 to 2 degrees C.). The control span selected is based on the tolerance of the plants P at different stages of development to the specific air temperature. It is critical that the air temperature does not vary throughout the growing area 13 so as to promote uniform plant growth and development.

No heating option is provided for the following reasons. When the lights 26 are on, the radiant energy from the lamps 26 heats the air temperature of the plant growing area 13 beyond the selected temperature control level, and so cooling is required to maintain the selected temperature control level. When the lights 26 are off, or during the dark period of the 24-hour cycle, plant growth and development is enhanced when the air temperature is controlled at a lower level than during the light period. This diurnal temperature cycle is achieved without the use of heating to maintain the desired air temperature control levels.

The use of a commercially available room air conditioner 30, modified to control the air temperatures to 50 degrees F., a wide temperature control span, and not including equipment to provide heating of the air temperatures in the plant growing area 13 significantly reduce the initial and maintenance costs of the plant chamber 14 and the electrical operational costs. These design features are significant considerations that impact the commercial viability of using controlled environmental chambers 14 for the production of pre-basic seed potato material.

Atmospheric Humidity System

The humidity level of the air in the growing area 13 of the plant chamber 14, as defined by percent relative humidity, is controlled by the use of the atmospheric humidity system 32 that includes a series of misting nozzles 28 and a high pressure (~80 psi) pump 88 that is activated when the relative humidity level goes below the selected level (FIG. 5). This provides a mist of deionized or distilled water from the reservoir 86 outside of the chamber 14 into the growing area 13 of the chamber 14 that quickly evaporates resulting in an increase in the percent relative humidity (humidification). The percent relative humidity is controlled over the range of 50 to 95 percent ±3 to 5 percent, depending on the stage of plant development.

No provisions are provided for decreasing the percent relative humidity (dehumidification) when the percent relative humidity is above the control set point. The percent relative humidity control set points are established to reflect the fact that plants P are insensitive to humidity levels above the control set point, but very sensitive to humidity levels below the control set point. These design features reduce the initial, maintenance, and operational costs without any negative impact on the growth and development of plants P in the growing area 13 of the chamber 14. These design features are significant considerations that have an important bearing on the commercial viability of using controlled environmental chambers 14 for the production of potato minitubers.

Nutrient and Water Delivery System

The nutrient and water delivery system 34 consists of a series of nozzles 112 that dispense a fine foliar spray onto the plants P growing in the chamber 14 of a nutrient solution from a reservoir 100 outside the chamber 14 when a low pressure (~30 psi) pump 102 is activated in accordance with a prescribed schedule (FIG. 6). The spray is a defined nutrient solution containing all the essential elements required to support plant growth and development. The pump activation schedule includes the frequency of the dispersion of the water and nutrient solution during a 24-hour period as well as the duration of the dispersion during any activation.

This system provides for both the automatic watering and fertilizing operations of the plants P growing in the plant chamber 14. Thus, a critical design feature of the water and nutrient delivery system 34 is the number and placement of the nozzles 112 to make certain that all the plants P in the growing area 13 of the chamber 14 receive adequate water and fertilization during the growing period.

The composition of the nutrient solution along with the frequency and duration of the spray are changed to coincide with the requirements of the plants P during the different stages of development while growing in the plant chambers 14 so as to optimize the growth and development process.

Computer Control System

The computer control system 20 monitors and records the environmental conditions in the growing area 13 of the plant chamber 14 and activates or deactivates the components involved in modifying the chamber environmental conditions (FIG. 1). The desired plant growing area environmental conditions are maintained at the specified set points via computer control system 20. The system 20 connects to the network switch 16, which in turn connects to the chamber control panel 19 on each of the chambers 14 via Ethernet cables 18.

An important and critical part of the computer control system 20 is the software package installed in the computer that contains the instructions for autonomously monitoring, controlling and recording the environmental conditions in the plant growing area 13 of the chamber 14. The control software package is written in the commercially available LabVIEW® (National Instruments, Dallas, Tex., USA) programming language. The software package is configured with the capability of monitoring, controlling and recording the environmental conditions of a number of chambers 14 from a single computer.

Each chamber control panel 21 contains the three FieldPoint® modules 70, 72, 74 (National Instruments, Dallas, Tex., USA) which are powered by a low voltage DC power supply (FIG. 3). The three modules include an Ethernet network interface module 70 (FP-1601) that functions as a microprocessor and interfaces between the network switch 16 and an eight channel analog-to-digital (A/D) conversion module 74 (FP-AI-100) that is the connection to the analog sensors 66, 68, and an eight channel digital output (DO) module 72 (FP-DO-400) that is the connection to the appropriate solid state relays 78, 80, 82, 84 to provide electrical power to activate the different components involved in maintaining the environmental conditions in the plant growing area 13 of the chamber 14. The three modules 70, 72, 74 are interconnected via the electrical and mechanical FieldPoint® terminal bases mounted on a DIN rail.

The electrical information generated by the FP-1601 module 70 is processed by the software in the computer of the system 20 to generate the data base for making a record of: (1) air temperature in the plant growing area 13, (2) percent relative humidity of the air in the plant growing area 13, (3) the light level just below the acrylic plastic ceiling 64 of the plant growing area 13, (4) an indication whether the lights 26 are on or off, (5) an indication of whether the nutrient solution pump 102 is on or off, and (6) an indication of whether the humidity pump 88 is on or off, at a selected point in time. The time interval between recording these parameters can be preselected from every minute to any desired interval, such as every 10 minutes. Thus, the record generated represents the status of the parameters at the time the data are presented to the computer software.

The signals generated by the FP-DO-400 module 72 are used to activate solid state relays 78, 80, 82, 84 to provide electrical power to turn on either one-third or two-thirds, or all of the fluorescent lamps 26, the fans 62 in the light cap 58, the air conditioning unit 30, and the pumps 88, 102 in the humidity and nutrient delivery systems 32, 34 respectively. The solid state relays 78, 80, 82, 84 are activated by a low voltage (~5 volts) DC signal, but are capable of providing 120 or 240 VAC and up to 18 amps of electrical power to the various load units.

Use of the commercially available FieldPoint® technology as part of the computer control system 20 greatly reduces the noise-to-signal ratio which is a common and serious problem in many computer control approaches. This design feature improves the reliability of the monitoring and control functions so critical to maintaining the desired environmental conditions in the plant growing area 13 of the chamber 14. This feature of the FieldPoint® modules 70, 72, 74 obviously reduces the possibility of control failures that could have serious negative consequences on the survival of plants P in the chamber 14 and on the commercial viability of the system 10 to produce the valuable plant materials.

The solid state relative humidity and temperature sensor 66 (Intercap® Humidity and Temperature Probe HMP 50, Vaisala Oyj., Helsinki, Finland) is located in the plant growing area 13 of the chamber 14. A 12 volt DC signal emanating from this sensor 66 provides the signal to the FP-AI-100 module 74 for monitoring and controlling the percent relative humidity and temperature of the air in the growing area 13 of the chamber 14. A silicon photodiode 68 is used to monitor the light level in the growing area 13 of the plant chamber 14 when the lights 26 are on. These sensors 66, 68 are located in the growing area 13 of the plant chamber 14 so as to provide a representative indication of the environmental conditions being monitored and controlled.

Plant Cultural Procedures

The cultural procedures used in growing pre-basic seed potato material that can be used to produce high quality, pathogen free seed for commercial potato growers are referred to in the scientific literature as originating from stem cuttings of "mother" plants. The significant difference between the reported literature and the one described is that the stem cuttings are grown in controlled environment chambers 14 rather than in a greenhouse or screenhouse. A diagrammatic description of the method of producing large quantities of the pre-basic seed potato material using the methods of this invention is given in FIG. 7.

Culture of Potato "Mother" Plants

Figure 7:
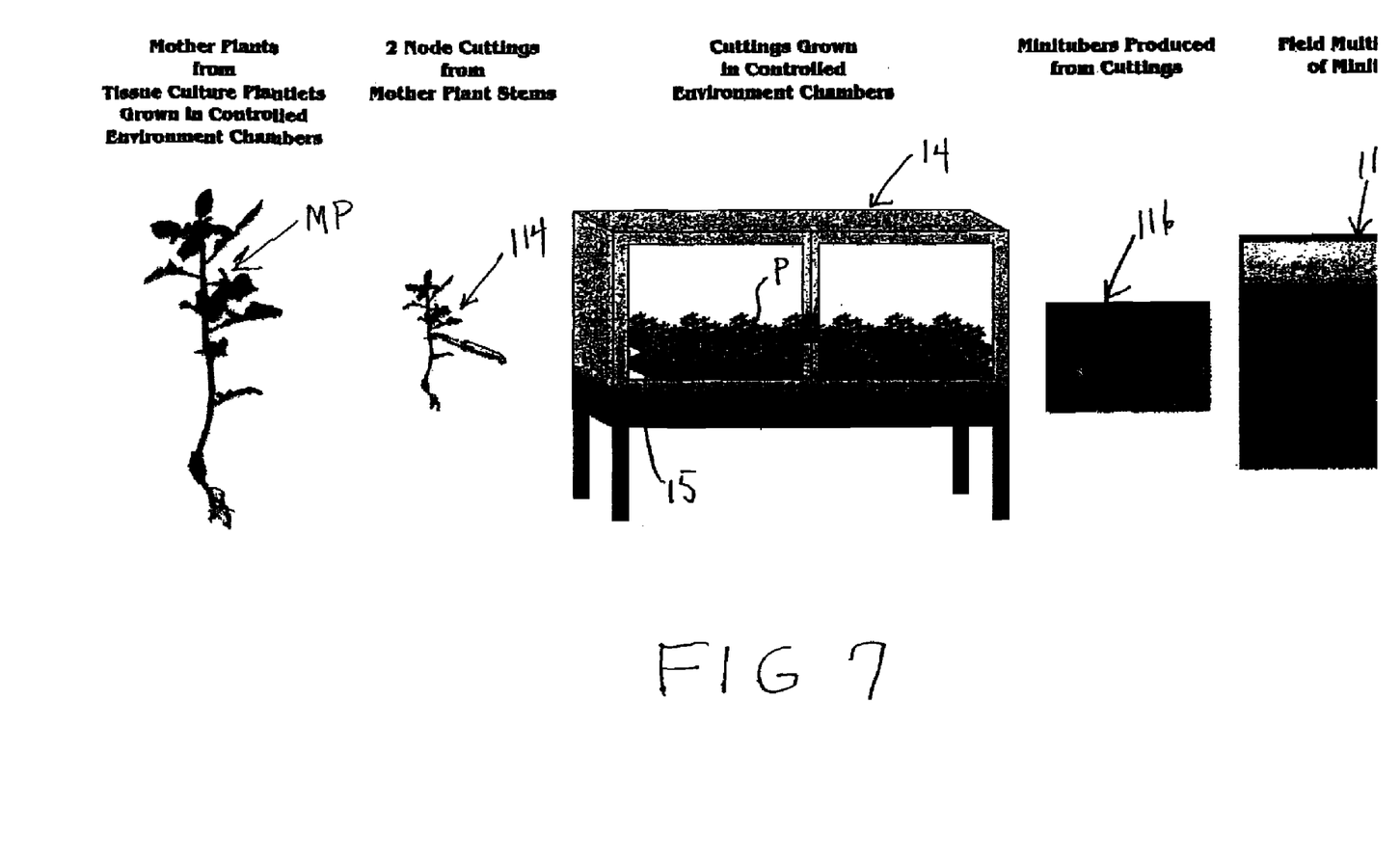
FIG. 7 is a representation of the process for propagating seed potatoes using the system of FIG. 1.

The potato "mother" plants MP are derived from tissue culture plantlets, obtained from organizations that routinely produce such plantlets of various potato varieties. Such plantlets have been extensively tested to assure that they are pathogen free. The tissue culture plantlets are planted in flats 15 containing a mixture of peat, coarse horticultural vermiculite, and perlite (1/2/1 parts by vol). The flats 15 are transferred to a controlled environment chamber 14. The air temperature in the growing area 13 of the chamber 14 is maintained at 77, ±3 degrees F. (25 degrees C.) during the light period and so that it does not exceed 68 degrees F. (20 degrees C.) during the dark period. The light period has a duration of 16 hours with a dark period of 8 hours. For the first week, the light level is at one-third of the fluorescent lamps (low light level), two-thirds of the fluorescent lamps 26 during the second week (medium light level), and at all the fluorescent lamps 26 (full light level) thereafter. Percent relative humidity of the air in the plant growing area 13 of the chamber 14 is maintained during the first five days so as to not go below 80 percent. After the five-day period, the percent relative humidity is maintained so as to not go below 60 percent during both the light and dark periods.

Foliar applications of a nutrient solution are applied at six-hour intervals during the light period and once during the dark period. The applications have a duration of 20 seconds. The nutrient solution has the following composition: $Ca(NO_3)_2.4H_2O$, 590 mg; $KNO_3$, 253 mg; $MgSO_4.7H_2O$, 246 mg; $KH_2PO_4$, 136 mg; $H_3BO_3$, 1.4 mg; $MnCl_2.4H_2O$, 1.0 mg; $CuSO_4.5H_2O$, 0.04 mg; $ZnSO_4.7H_2O$, 0.1 mg; $MoO_3$, 0.008 mg; Iron chelate (14% $Fe_2O_3$), 50 mg; per liter of distilled water, adjusted to a pH of 5.5 with 0.05 N $H_2SO_4$.

This plant culture program encourages and stimulates stem growth of the "mother" plants MP rather than tuberization. After approximately 4 weeks the "mother" plants MP will have stems 20 to 30 cm long. These stems are made into cuttings 114 of about 5 cm, each cutting 114 having at least one node using sterile cutting tools. After removal of the stems, the mother plants are continued to be cultured in the controlled environment so that repeated "crops" of stem cuttings 114 can be made from the same "mother" plant MP since the environmental conditions, particularly the length of the light period, keep the plants P in a vegetative condition rather than production of tubers. In this way a large number of cuttings 114 can be made from a minimum of tissue culture plantlets resulting in a considerable reduction in operational costs.

Culture of Cuttings for the Production of Basic Seed Potatoes

The lower part of the stem cuttings 114 taken from the "mother" plants MP are immersed for 15 minutes in a solution that stimulates the development of adventitious roots. The composition of this root stimulating solution is: 20 ppm of indole-3-butyric acid (IBA), 380 ppm of 1-napthaleneacetic acid (NAA), 400 ppm of thiamin hydrochloride (B-1), and 1000 ppm of $KH_2PO_4$. The stem cuttings 114 are then planted, using sterile utensils, into trays 15 containing a rooting material of peat, coarse horticultural vermiculite, and perlite (1/2/1 parts by volume). The cuttings 114 are spaced at 2 inch centers (5 cm) in the trays 114.

The trays 15 with the cuttings 114 are placed into the controlled environment chambers 14. The air temperature in the plant growing area 13 of the chambers 14 is controlled to maintain 68, ±4 degrees F. (20 degrees C.) during the light period and so that it does not exceed 68 degrees F. (20 degrees C.) during the dark period. The light period has a duration of 12 hours with a dark period of 12 hours. For the first week, the light level is at one-third of the fluorescent lamps 26 (low light level). During the second week the light level is increased to two-thirds of the fluorescent lamps 26 (medium light level). At the end of the two weeks, the light level is increased to all of the fluorescent lamps 26 (full light level). Percent relative humidity of the air in the plant growing area 13 of the chamber 14 is maintained during the first five days so as to not go below 80 percent during both the light and dark periods. During the next five days, the percent relative humidity is maintained so as to not go below 70 percent during both the light and dark periods. After the 10-day period, the percent relative humidity is maintained so as to not go below 50 percent during both the light and dark periods.

Foliar applications of a nutrient solution are applied at six-hour intervals during the light period and once during the dark period. The applications having a duration of 20 seconds. The nutrient solution has the following composition: $Ca(NO_3)_2.4H_2O$, 590 mg; $KNO_3$, 253 mg; $MgSO_4.7H_2O$, 246 mg; $KH_2PO_4$, 150 mg; $K_2SO_4$, 68 mg; $H_3BO_3$, 1.4 mg; $MnCl_2.4H_2O$, 1.0 mg; $CuSO_4.5H_2O$, 0.04 mg; $ZnSO_4.7H_2O$, 0.1 mg; $MoO_3$, 0.008 mg.; Iron chelate (14% $Fe_2O_3$), 50 mg; per liter of distilled water, adjusted to a pH of 5.5 with 0.1 $NH_2SO_4$.

At the end of the three week growing period and for the following five weeks, the air temperature in the plant growing area 13 of the chamber 14 is maintained at 68±3 degrees F. (20 degrees C.) during the light period and 50±3 degrees F. (10 degrees C. during the dark period. The light level is provided by all the fluorescent lamps 26. The duration of the light period is 12 hours and the dark period is 12 hours.

A foliar application of an aqueous mixture of 15 ppm of ancymidol and 10 ppm of kinetin is made during the third week and the fourth week to enhance initiation of tuberization and development of tubers 116. The tubers 116 are harvested after a growing period of seven to eight weeks.

It should be pointed out that the specific culturing procedures defined in this invention are provided as a cultural example and may need to be modified for specific potato cultivars in order to optimize the number and size of the tubers harvested at the end of the growing period. The modifications would be primarily related to the frequency and duration of the foliar applications of the water and nutrient solution and the composition of the foliar application of the aqueous solution used to enhance tuberization.

After 50-60 days from the start of the growth cycle, depending on the specific potato cultivar, the tubers 116 are harvested and placed in storage under conditions required to break the tuber dormancy condition and sprout when planted in the field. The duration and storage conditions vary depending on the potato cultivar.

The tubers 116 produced in the controlled environment chambers 14 are subsequentially planted in the field 118 for the initial multiplication. The production fields are closely monitored and treated as required to control disease and insect infestation of these fields. The specific controlled treatments depend on the geographical location of the fields and the nature of the disease or insect infestations. The tubers 116 harvested from these field plantings are termed "FG-1" seed potato stocks and, for example, would compare to the "Elite Foundation Seed" produced by the Wisconsin Seed Potato Certification program. The FG-1 tubers 116 are planted in the field 118 to obtain a sufficient quantity of tubers 116 that can be sold as seed stock material to potato growers. The tubers 116 harvested from the second field multiplication are termed "FG-2" seed potato stocks. The FG-2 tubers 116 are comparable in quality to traditional foundation seed available to seed growers but would be labeled as "certified seed".

Of critical importance to the efficiency of the method set forth above is the ability of the system 10 to continuously monitor and record the temperature, humidity and presence of light in each chamber 14 by means of the sensors 66, 68, and then reactively and continuously control the lighting, temperature humidity and nutrient delivery relays 78, 80, 82, 84 and their associated systems 24, 28, 32, 34 depending on the particular potato cultivar of interest.

While the invention has been described with reference to a preferred embodiment, those skilled in the art will appreciate that certain substitutions, alterations and omissions may be made without departing from the spirit thereof. Accordingly, the foregoing description is meant to be exemplary only and should not be deemed limitative on the scope of the invention set forth with the following claims.

I claim:

1. A plant growing system for developing potato plants that produce minitubers comprising:

at least one automatically controlled environment chamber means for holding and supporting growth of potato plants over an entire life cycle, the chamber means including temperature, humidity and light sensor means, a lighting means for establishing light and dark periods of exposure having a number of fluorescent lamps located above the potato plants and separated therefrom by a substantially transparent divider, an air temperature means including an air conditioner for creating a variable temperature uniformly throughout the chamber means, an atmospheric humidity means, a nutrient and water delivery means for fertilizing and irrigating the potato plants, and a computer means for automatically and continuously monitoring and controlling the lighting, air temperature, atmospheric humidity and nutrient and water delivery means;

the system enables development of both tissue culture plantlets that produce mother plants, and stem cuttings from the mother plants into minitubers; wherein the chamber means further includes maintaining an air temperature of 68-72 degrees F. during a light period of 12 hours and an air temperature that does not exceed 68 degrees F. during a dark period of 12 hours for a first week throughout which the stem cuttings are illuminated at a low level in which one-third of the fluorescent lamps are on, for a second week at a medium light level in which two-thirds of the fluorescent lamps are on and for a third week at a full light level in which all fluorescent lamps are on and further maintaining an air temperature of 65-71 degrees F. during the light period and an air temperature of 47-53 degrees F. during the dark period for about five weeks following the third week of culturing and the computer means periodically records environmental parameters in the chamber means.

2. The system of claim 1, wherein the chamber means is defined by a housing having a top panel, a bottom panel, a back panel, opposite end panels, a substantially transparent acrylic divider panel spaced beneath the top panel, a perforated drain pan spaced above the bottom panel for supporting trays of the potato plants and a movable door arrangement at a front portion thereof, the housing forming a light cap for holding the fluorescent lamps therein and a plurality of ventilating fans on the back panel and the front portion, a plant growing area between the divider and the drain pan for holding the trays of potato plants in a single layer, and a drain area located between the drain pan and the bottom panel.

3. The system of claim 2, wherein the temperature, humidity and light sensors are located in the plant growing area.

4. The system of claim 1, wherein the computer means controls the percentage of fluorescent lamps that are turned on during the light periods of exposure.

5. The system of claim 2, wherein the chamber means includes control panel means having signal processing module means in communication with a temperature control relay, a humidity control relay, a water and nutrient supply relay and a light control relay for providing electrical power to the fluorescent lamps, the air conditioner, the fans, and pumps in the humidity means and water and nutrient means.

6. The system of claim 5, wherein the computer means responsive to the module means provides a record at a selected point in time of the air temperature in the plant growing area, the percent of relative humidity of the air in the plant growing area, the light level immediately below the divider panel, an indication whether the lights are on or off, and an indication of whether the pumps are on or off.

7. The system of claim 1, wherein the computer means causes air temperature to be maintained at 50-86 degrees F., and causes relative humidity to be maintained at 47%-100%.

* * * * *